(12) United States Patent
Carrillo

(10) Patent No.: US 6,893,393 B2
(45) Date of Patent: May 17, 2005

(54) GUIDEWIRE LOCKING DEVICE AND METHOD

(75) Inventor: Oscar Carrillo, Attleboro, MA (US)

(73) Assignee: Boston Scientific SciMed., Inc., Maple Grove, MN (US)

( * ) Notice: Subject to any disclaimer, the term of this patent is extended or adjusted under 35 U.S.C. 154(b) by 233 days.

(21) Appl. No.: 10/370,173

(22) Filed: Feb. 19, 2003

(65) Prior Publication Data

US 2004/0162465 A1 Aug. 19, 2004

(51) Int. Cl.⁷ .............................. A61B 1/00
(52) U.S. Cl. .................. 600/154; 600/104; 600/153
(58) Field of Search ............................ 600/104, 106, 600/153, 154

(56) References Cited

U.S. PATENT DOCUMENTS

| | | | |
|---|---|---|---|
| 4,715,360 A | * 12/1987 | Akui et al. | 600/154 |
| 5,320,602 A | 6/1994 | Karpiel | |
| 5,397,302 A | 3/1995 | Weaver et al. | |
| 6,200,262 B1 | * 3/2001 | Ouchi | 600/154 |
| 6,746,466 B2 | * 6/2004 | Eidenschink et al. | 606/194 |
| 2002/0177869 A1 | 11/2002 | Eidenschink et al. | |

FOREIGN PATENT DOCUMENTS

WO    WO 99/59664    11/1999

* cited by examiner

Primary Examiner—Beverly M. Flanagan
(74) Attorney, Agent, or Firm—Fay Kaplun & Marcin, LLP

(57) ABSTRACT

A locking device for a maintaining an elongated member at a selected place within a body lumen comprises a substantially rigid body including an attachment portion adapted to be coupled to a distal portion of a medical instrument wherein, when in an operative position, the distal portion of the medical instrument is received within the body lumen and an angled head coupled to the substantially rigid body, the angled head being configured to overlie an access port of the medical device when the attachment portion is coupled to the distal portion of the medical device in a predetermined configuration in combination with a plurality of locking features extending from the angled head to immobilize a section of the elongated member relative to the medical device and a locking arm extending from the locking device so that, when the attachment portion is coupled to the medical device, the locking arm extends between the access port and the locking features to guide the elongated member from the access port to the locking features along a desired path.

26 Claims, 10 Drawing Sheets

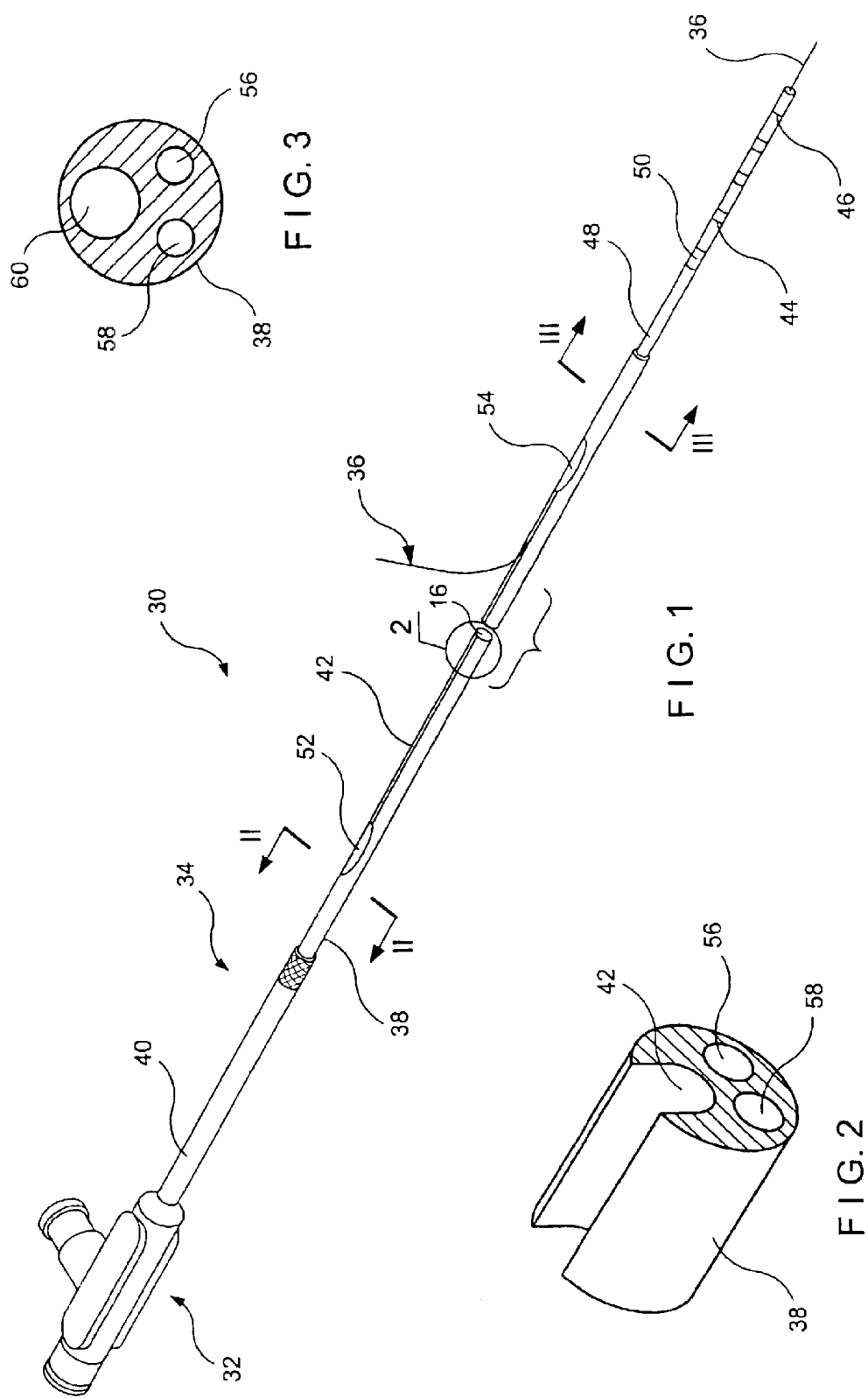

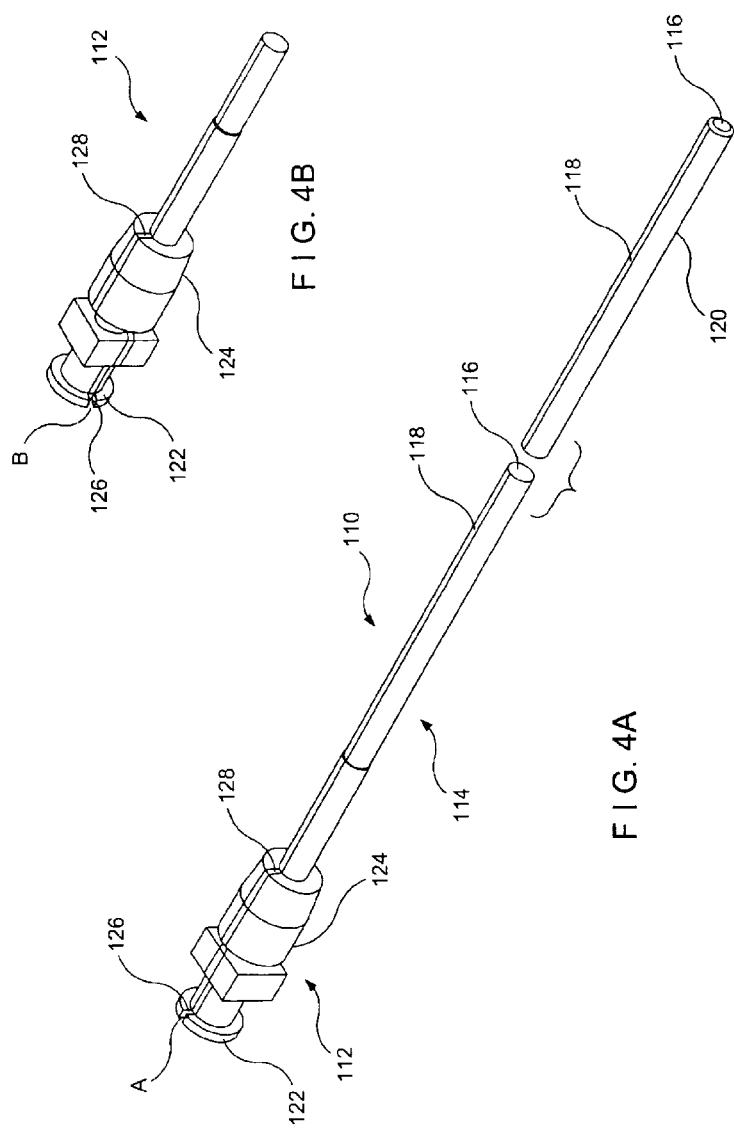

FIG. 6

GUIDEWIRE LOCKING DEVICE AND METHOD

BACKGROUND INFORMATION

Endoscopic procedures to treat abnormal pathologies of the alimentary canal and the biliary tree are becoming increasingly common. Endoscopes are often used in these procedures to facilitate access to biliary, hepatic and pancreatic ducts, in addition to the larger alimentary passages. The endoscope itself can only provide access to the general area adjacent to the smaller ducts and navigation of the ducts themselves must be carried out using smaller devices, such as catheters and guide wires in conjunction with fluoroscopy. Targeted delivery of therapeutic agents and surgical procedures within the ducts is typically carried out using catheters.

Methods and devices for using catheters to access the biliary tree are described in U.S. Pat. No. 5,397,302 to Weaver et al., and in U.S. Pat. No. 5,320,602 to Karpiel, the disclosures of which are herein incorporated by reference in their entirety. In a general process, treatment of a patient's biliary tree involves introducing an endoscope in the mouth of a patient, and guiding the distal end of the endoscope through the alimentary tract until a distal opening of the endoscope is adjacent to a targeted area to be treated. Additional devices such as catheters may be introduced through the endoscope to the target area, to perform whatever procedure is required to treat the abnormal pathology. In one procedure, a distal end of the catheter is guided through the orifice of the papilla of vater, which leads into the common bile duct and the pancreatic duct. The catheter is inserted through a lumen of the endoscope, so that it emerges in the ducts at the distal end of the endoscope.

A guide wire may be used in conjunction with the catheter to facilitate accessing the desired location. The guide wire is inserted in an opening at the proximal end of the catheter, and is guided through the catheter until it emerges from the catheter's distal end. The guide wire is then pushed to the target in the common bile duct, and the catheter is advanced over the guide wire until the catheter's distal end reaches the desired target position. A catheter may be selected to deliver contrast media to the target area, for fluoroscopic visualization of anatomical detail within the duct. Different catheters specialized for different functions may be necessary to treat the target area that has been visualized, and a catheter exchange may need to be performed. An exchange involves removing the first catheter and replacing it with a second catheter, without displacing the guide wire during the procedure. If the guide wire is displaced, the guide wire must be redirected through the body to the target area, in a difficult and time consuming procedure.

In a conventional procedure, the physician must grasp the proximal end of the guide wire with one hand to immobilize it, and must perform the catheter exchange with the other hand. This procedure is difficult and often results in displacing the guide wire. In addition, it is often necessary to hold in place more than one guide wire at the same time. Manually holding multiple guide wires is extremely difficult when conventional methods and devices are used, since the surgeon has to manually hold the guide wires in place while at the same time replacing one or more catheters. Additional personnel is often required to carry out the procedure using conventional methods.

SUMMARY OF THE INVENTION

The present invention is directed to a locking device for maintaining an elongated member at a selected place within a body lumen comprising a substantially rigid body including an attachment portion adapted to be coupled to a distal portion of a medical instrument wherein, when in an operative position, the distal portion of the medical instrument is received within the body lumen and an angled head coupled to the substantially rigid body, the angled head being configured to overlie an access port of the medical device when the attachment portion is coupled to the distal portion of the medical device in a predetermined configuration in combination with a plurality of locking features extending from the angled head to immobilize a section of the elongated member relative to the medical device and a locking arm extending from the locking device so that, when the attachment portion is coupled to the medical device, the locking arm extends between the access port and the locking features to guide the elongated member from the access port to the locking features along a desired path.

The present invention is further directed to a locking device for maintaining a position within a body lumen of a first elongate member relative to a flexible endoscope while a second elongate member is withdrawn from the body lumen, the locking device comprising a mounting mechanism for selectively coupling the locking device to a distal end of the endoscope and an angled head which, when the mounting mechanism is coupled to the endoscope in a predetermined configuration, overlies an opening at a distal end of the endoscope to a working channel of the endoscope in combination with a plurality of locking features extending from the angled head to immobilize a portion of the first elongate member relative to the endoscope and a locking arm extending from the angled head between the opening at the distal end of the endoscope and the locking features to limit movement of a portion of the first elongate member between the opening and the locking features.

The present invention is further directed to a method of performing a medical procedure, comprising the steps of inserting an endoscope into a body lumen and inserting a distal end of a first elongate member into the lumen via the access port so that a proximal portion of the first elongate member extends from proximally from the access port in combination with the steps of providing a locking device at a distal end of the endoscope, immobilizing a portion of the first elongate member relative to the endoscope by engaging a first locking feature of the locking device with the first elongate member and engaging a locking arm of the locking device with the first elongate member to direct the first elongated medical member along a first predetermined path from the distal end of the endoscope to the first locking feature.

BRIEF DESCRIPTION OF DRAWINGS

FIG. 1 is a perspective view of a catheter according to an embodiment of the present invention, having a partially open guidewire lumen;

FIG. 2 is a fragmentary perspective view of the catheter shown in FIG. 1, showing a cross section along plane II;

FIG. 3 is a cross sectional view of the catheter shown in FIG. 1, taken along line III—III;

FIGS. 4 and 4A are perspective views showing an endoscope sheath assembly according to an embodiment of the present invention;

Figure 6:
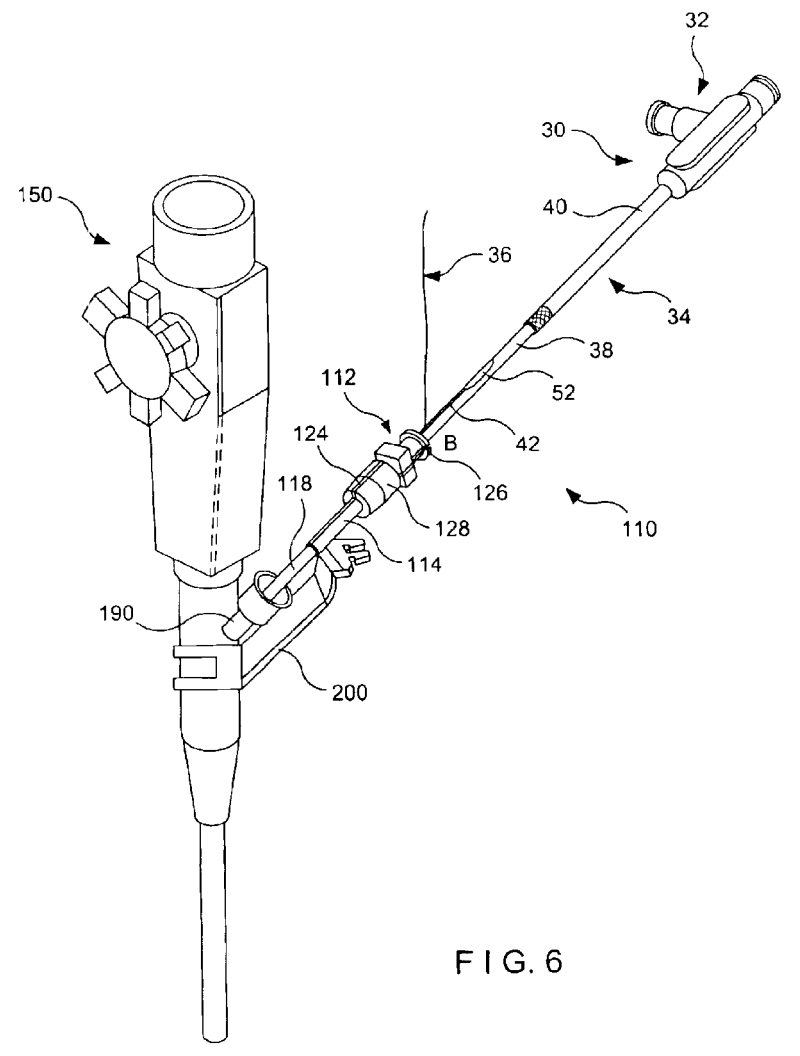

FIG. 6 is a perspective view showing a catheter assembly mounted on an endoscope, according to an embodiment of the present invention;

FIG. 7A shows a first side view of a guide wire locking arm according to an embodiment of the present invention;

FIG. 7B shows a front view of the locking arm of FIG. 7a;

FIG. 7C shows a second side view of the locking arm of FIG. 7A;

DETAILED DESCRIPTION

Figure 5:
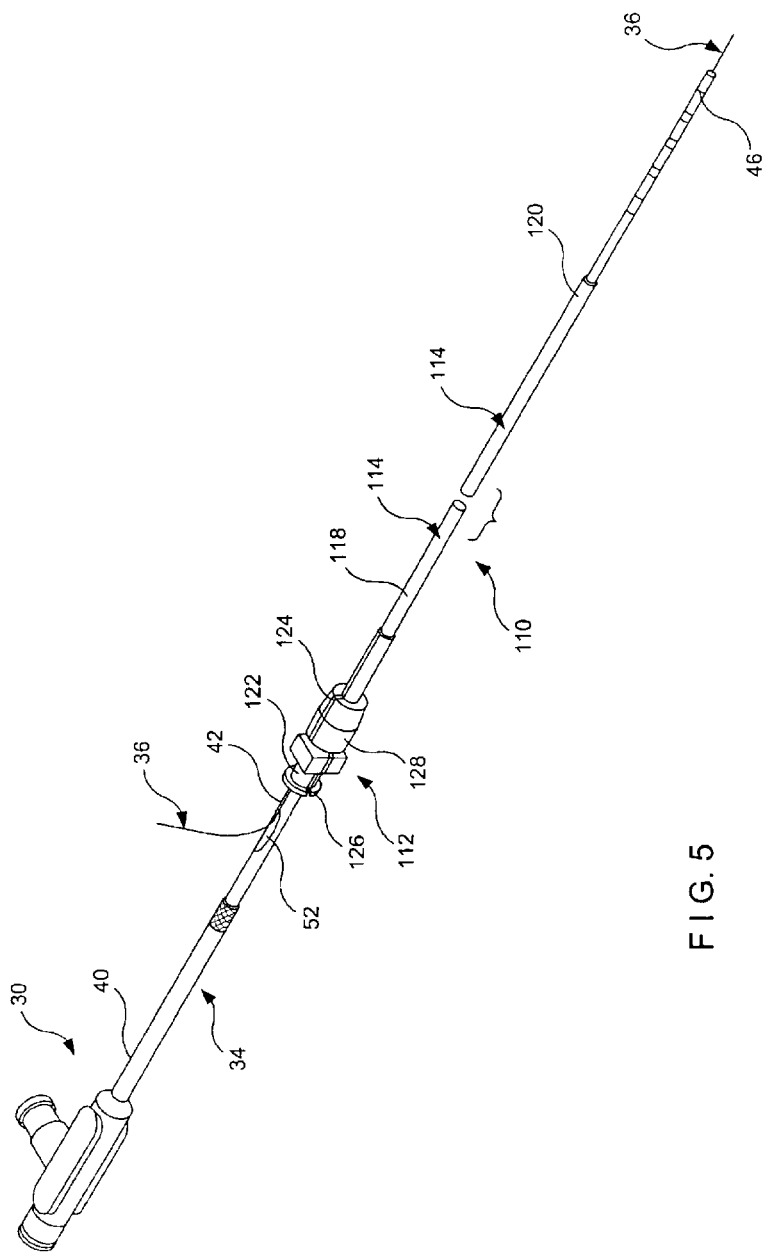
FIG. 5 is a perspective view showing a catheter connected to an endoscope sheath assembly according to the present invention.
Figures 7A, 7B, 7C:
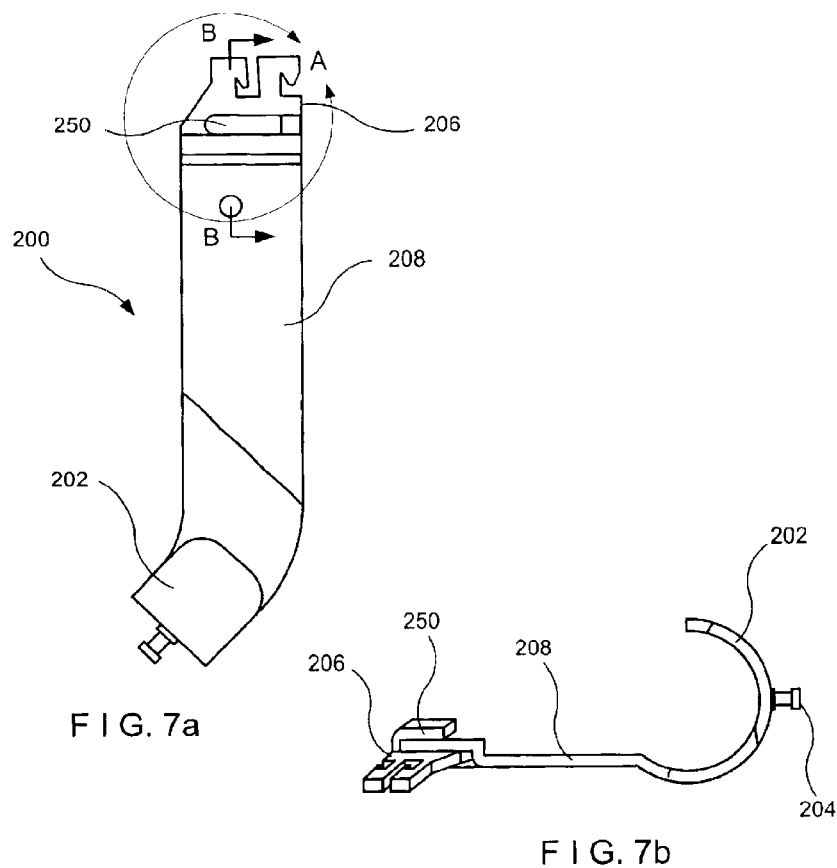

FIG. 1 shows an exemplary embodiment of a catheter assembly 30 according to the present invention for use in accessing targeted anatomical regions through, e.g., the alimentary canal. The present invention incorporates features that allow rapid exchange of one or more catheters by a single operator. The catheter of the present invention allows shorter length guide wires to be used, resulting in procedures which require fewer medical personnel, are less time consuming, and less costly. Additionally, the present invention is adaptable to a variety of devices for catheter procedures within the alimentary canal or any other body lumen.

The catheter assembly 30 includes a catheter hub assembly 32 and a catheter 34 with a guide wire lumen 60 extending therethrough. As shown in FIGS. 2 and 3 a guide wire 36 may be inserted therein. The catheter 34 includes a shaft 38 which has a proximal end 40, a channel 42, a distal tip region 44, a distal end 46 and several internal lumens described in greater detail below. The catheter hub assembly 32 which is operably connected to a proximal end 40 of the shaft 38 may preferably be configured to couple to ancillary devices allowing access to one or more lumens within the shaft 38. In different embodiments, more than one guidewire lumen 60 may be provided in catheter assembly 30, to be used with additional guide wires.

The shaft 38 may preferably be a generally tubular member having a substantially uniform outer shape at the proximal end 40. As would be understood by those of skill in the art, the shaft 38 may be sized for slidable passage through the lumen of an endoscope or through a body lumen and may preferably be formed in an extrusion process of, e.g., a polymeric material. In one embodiment, the preferred polymeric material may be polytetrafluoroethylene, polyether block amide, nylon or a combination or blend of these. Catheters that are contemplated for used with the present invention include, but are not limited to, cannulas, sphincterotomes, cytology devices, and devices for stone retrieval and stent placement. The shaft 38 may further include a distal taper 48 tapering to the distal tip region 44. As would be understood by those skilled in the art, the distal tip region 44 may include high contrast, color-coded distal markers 50 and may be radiopaque for fluoroscopic visualization of the distal tip region 44 during catheter procedures.

The guide wire lumen 60 extends through the catheter 34 from a proximal end to a distal end thereof with a channel 42 forming a portion thereof extending between a channel proximal end 52 and a channel distal end 54. The channel 42 serves to contain, but not necessarily constrain, the guide wire 36 therein. The channel 42 allows radial removal of the guide wire 36 therefrom via a slot extending between the walls of the channel 42 and opening an interior of the guide wire lumen 60 to an outside of the catheter 34. As shown in FIG. 2, the channel 42 is substantially "U" shaped. However, the channel 42 may alternatively be shaped substantially like a letter "C" with sides of the channel extending inward from a maximum diameter to partially close the slot between the walls of the channel 42. The "C" shape of the channel may increase the overall strength of the shaft 38 to resist bending in the direction of the opening. This increased strength of the shaft 38 may then allow for greater force to be used in pushing the catheter 34 into the body.

In one embodiment, the channel 42 is sufficiently large to allow unhindered radial removal of the guide wire 36 from the channel 42 via the slot extending between the walls thereof. As shown in FIG. 2, the slot opening the channel 42 to an outside of the catheter 34 may be formed to be substantially equal in size to or slightly larger than a diameter of a guide wire to be used with the catheter 34, as described in greater detail below. This size selection allows deliberate removal of guide wire 36 from channel 42 while restraining the guide wire 36 from falling out of the guide lumen 60. Although it is recognized that the channel proximal end 52 may be located at any location distal of the proximal end 40 of the shaft 38, the channel distal end 54 is preferably located between 10 and 40 cm from the distal end 46 of the catheter shaft 38. The channel distal end 54 may more preferably be located between 20 and 30 cm and, most preferably, approximately 25 cm from the distal end 46.

As shown in FIGS. 1, 2 and 3, in a region proximal to the channel proximal end 52, the guide wire lumen 60 is completely sealed from an outside of the catheter 34. As described above and described more fully below, the portion of the guide wire lumen 60 between the channel proximal and distal ends 52, 54, respectively, (i.e., the channel 42) is open to the outside of the catheter 34 via a slot. The catheter 34 according to this exemplary embodiment also includes ancillary lumens 56 and 58 which may be used for a variety of medical purposes. As would be understood by those of skill in the art, the ancillary lumens 56 and 58 may preferably extend longitudinally between the proximal end 40 and the distal end 46 of the shaft 38 and may be used, for example, as injection lumens for high contrast media for visualization of a desired anatomical region. Additionally or alternatively, the ancillary lumens 56 and 58 may, for example, be used for or serve as part of another ancillary device, such as a cutting wire or a retrieval balloon, etc.

The guide wire lumen 60 preferably extends longitudinally between the proximal end 40 and the distal end 46 of the shaft 38, and is sized to receive the guide wire 36 slidably therein. In one example, the guide wire 36 has a diameter of between 0.6 mm and 0.9 mm. As would be understood, the guide wire lumen 60 may be formed integrally with the catheter shaft 38, as shown in FIG. 3 or, alternatively, may be formed as a separate tubular member coupled to the catheter shaft 38. In one preferred embodiment, the guide wire lumen 60 is a tubular member which is located proximate the distal end 46 of the shaft 38. However, the guide wire lumen 60 may be formed anywhere else along the shaft 38, may comprise an extension of the shaft 38 coupled to the distal end 46 thereof, or may run the entire length of the shaft 38, as would be understood by those skilled in the art.

In use, after a distal end of guide wire 36 has been positioned at a desired location within the body, the physician simply inserts a proximal end of the guide wire 36 into the guide wire lumen 60 via an opening at the distal end 46 of the catheter 34 and slides the catheter 34 distally along the guide wire 36. During the maneuver, the physician may grip the portion of the guide wire 36 extending distally of the distal end 46 of the catheter 34 to maintain the distal end of the guide wire 36 in the desired position within the body. When the proximal end of the guide wire 36 has reached the open channel 42, the proximal end of the guide wire is deflected out of the guide wire lumen 60 through the slot extending between the walls of the channel 42. The physician may then grasp the proximal end of the guide wire 36 and continue to slide the catheter 34 along the guide wire 36 until the distal end 46 of the catheter 34 reaches the desired location within the body. As the guide wire 36 is received within the guide wire lumen 60 only along a short portion of the length of the catheter 34, those skilled in the art will understand that the physician may at all times maintain his grasp on an exposed portion of the guide wire 36 to maintain it in position without the need for guide wire extenders, etc.

If during the procedure the catheter 34 is to be exchanged for another catheter as may be required when, for example, placing of multiple stents within a patient, the physician simply draws the catheter 34 proximally along the guide wire 36 while grasping the proximal end of the guide wire 36. When the distal end of the catheter 34 exits the body, the physician may then grasp the portion of the guide wire 36 extending distally of the catheter 34 and remove the catheter 34 completely from the guide wire 36. The loading process described above may then be repeated for the new catheter. Those skilled in the art will understand that the new catheter may be constructed as described above in regard to the catheter 34 or may be constructed in accord with any known catheter construction. The physician may also exchange the guide wire 36 while maintaining the catheter 34 in a desired position within the body, by performing the following steps. First, while grasping the proximal end of the catheter 34 to maintain the distal end 46 of the catheter 34 in the desired position within the body, the physician draws the guide wire 36 distally out of the guide wire lumen 60 and removes it from the body. Then, the new guide wire 36 is inserted into the guide wire lumen opening at the proximal end of the catheter 34 and is fed through the guide wire lumen 60, past the channel proximal end 52, through the channel 42 so that it passes into the portion of the guide wire lumen 60 extending distally of the channel distal end 54 and exits the distal end 46 of the catheter 34.

If catheter 34 later needs to be exchanged while maintaining the guide wire 36 in position, the physician grasps the proximal end of the guide wire 36 to maintain it in position and slides the catheter 34 proximally along the guide wire 36 until the channel proximal end 52 is located outside the body. The physician may then grasp the guide wire 36 from the channel 42 and draw the proximal end of the guide wire 36 distally through the proximal portion of the guide wire lumen 60, while holding the distal portion of the guide wire 36 stationary to maintain the position of the distal end of the guide wire 36. When the proximal end of the guide wire 36 has been removed from the guide wire lumen 60, the catheter 34 may be drawn proximally from the body with the guide wire 36 sliding out of the channel 42. When the distal end of the catheter 34 is outside the body, the physician grasps the portion of the guide wire 36 extending distally of the distal end 46 of the catheter 34 and withdraws the catheter 34 from the guide wire 36.

The endoscope and catheter according to the present invention may be used, for example, in the treatment of pathologies within a patient's biliary tree. Generally, for the treatment of pathologies within the patient's biliary tree an endoscopic biliary procedure is performed. During an endoscopic biliary procedure, the endoscope is introduced into the mouth of a patient and guided down the patient's alimentary canal through the esophagus, the stomach, and past the pyloric sphincter of the stomach into the duodenum. Once in the duodenum, the endoscope may be guided to a position in which its distal end is proximate to the target area (e.g., the papilla of vater). Throughout the procedure the proximal end of the endoscope extends and remains outside the mouth of the patient, where it is accessible to the physician using the device.

FIG. 4 shows an exemplary embodiment according to the present invention of an endoscope sheath assembly 110. The endoscope exchange sheath assembly 110 may include a two-piece hub assembly 112, a sheath 114 and a defining lumen 116. The defining lumen 116 includes a slit 118 extending longitudinally over its length, terminating at a distal end 120 of the sheath assembly 110. The two-piece hub assembly 112 has a proximal hub portion 122 and a distal hub portion 124, axially rotatable relative to one another. The proximal hub portion 122 has a proximal slit 126 and the distal hub portion 124 has a distal slit 128. When the proximal hub portion 122 is in a position "A", as shown in FIG. 4, the slit 118 is in alignment with the proximal and distal hub slits 126 and 128. This allows a guide wire to be radially slid into or out of the sheath assembly 110. In FIG. 4A the proximal hub portion 122 is shown in a position "B", rotated with respect to distal hub slit 128. In this position proximal slit 126 is out of alignment with distal slit 128, so that the guide wire cannot be removed. As would be understood by those of skill in the art, the proximal hub portion 122 may be set to position "B" when radial guide wire movement is not desired and returned to position "A" when removing the guide wire.

FIG. 5 shows an exemplary embodiment according to the present invention of a catheter assembly 30 as shown in FIG. 1, inserted through an endoscope sheath assembly 110 as shown in FIG. 4. The catheter 34 is inserted through the sheath assembly 110, extending distally from the sheath distal end 120, with the guide wire 36 received within the guide wire lumen 60 and passing through the channel 42 thereof to the shaft distal end 46. The guide wire 36 passes through that portion of the catheter 34 which is received within and engaged by the hub assembly 112. In this embodiment, to perform a catheter exchange as described above, the physician must first rotate the proximal and distal hub portions, 122, 124, respectively, from the locked position "B" to the open position "A". Thereafter, the physician performs the same steps described above to perform the rapid exchange, except that the guide wire 36 must be drawn out of the slit 118 after it has been removed from the channel 42 so that the physician may grasp it.

Prior to positioning the endoscope within the patient, the catheter assembly 30 is fed onto the guide wire 36. Specifically, a distal end of the guide wire 36 is inserted into the guide wire lumen 60 via the channel distal end 54 and is passed therethrough to the catheter distal end 46. The guide wire 36 may be fed into the guide wire lumen 60 through channel 42 of catheter 34, and further to the distal end 46. From there, the guide wire 36 is advanced through the endoscope and extended from the distal end thereof to be advanced through the body lumen of the patient to the target area, e.g., using flouroscopy to guide the guide wire. Once guide wire 36 has been positioned at the target area, the catheter assembly 30 is inserted into the endoscope and advanced therethrough along the guide wire 36 until the distal end 46 of the catheter 34 extends distally beyond the distal end of the endoscope. The catheter 34 is then further advanced distally along the guide wire 36 until the distal end 46 of the catheter 34 is in a desired position within the patient's body.

Once the distal end 46 of the catheter 34 has been positioned at the target area, medical procedures may be performed using the catheter 34. For example, contrast media such as radiopaque dye may be injected through the ancillary lumens 56 or 58 into the common bile duct for visualization of the duct. After the desired catheter procedure has been completed, the catheter assembly 30 may be exchanged or removed from the endoscope, leaving the guide wire 36 in position for other guide wire procedures to be carried out as described above.

Specifically, to remove the catheter 34 from the endoscope when using a catheter 34 according to the described exemplary embodiment, a proximal end of the guide wire 36 is grasped to prevent longitudinal movement thereof while the catheter 34 is retracted through the endoscope. Retraction of the catheter 34 while leaving the guide wire 36 in position within the patient is possible because the guide wire 36 is received within the catheter 34 for only the short distance between the channel distal end 54 and the catheter's distal end 46. Guide wire 36 is thus contained within the catheter 34 only along this short length, and a guide wire 36 double the length of the catheter 34 is not required to facilitate catheter exchanges. Thus a single operator may use one hand to grasp the portion of the guide wire 36 extending proximally from the catheter 34, while drawing the catheter 34 proximally from the body lumen with the other hand. When the distal 46 end of the catheter 34 is drawn out of the body, the operator may grasp the portion of the guide wire 36 extending distally of the distal end 46 of the catheter 34 and remove the catheter 34 completely from the guide wire 36. The accessible portion of the guide wire 36 is then held by the operator, while withdrawing the remaining portion of the catheter 34 completely over the guide wire 36. For example, this procedure may be carried out using a Rapid Exchange® catheter manufactured by Boston Scientific Corporation. According to embodiments of the present invention, the holding of the guide wire 36 is assisted by a guidewire locking device 200, which holds the guide wire 36 in place and frees the operator's hands for other tasks.

For example, if a stent (not shown) having an outside diameter larger than which can be accomodated by the sheath is to be advanced over the guide wire 36, the sheath assembly 110 may have to be exchanged. Alternatively, It may also be necessary to exchange both the sheath assembly 110 and the catheter assembly 30 simultaneously. In both cases a single operator is able to access a portion of the guide wire 36 between the distal end 46 of the catheter 34 and the proximal end of the endoscope 150, and to hold that portion of guide wire 36 in place while the catheter assembly 30 is completely removed or disengaged from the guide wire 36. As described below, a guidewire locking device 200 may be employed to lock in place a section of the guide wire 36, so that the operator is free to handle the stents, the catheter 34 and the sheath assembly 110 without displacing guide wire 36 from the target region in the patient's body.

FIGS. 7A–7C and 8 a guidewire locking device 200 according to the present invention. An attachment portion 202 is provided at one end of locking device 200, so that it may be securely connected to a medical tube such as endoscope 150. Attachment portion 202 may take different forms, as long as it provides a secure attachment to endoscope 150. For example, the exemplary embodiment shown includes an attachment portion 202 that is semicircular and is adapted to fit partially around the barrel of the endoscope 150. As will be understood by those skilled in the art, the diameter of the curved attachment portion 202 is selected to substantially match that of the endoscope 150 being used. Different versions of the locking device 200 may be provided, sized to fit different endoscopes as would be understood by those of skill in the art. Alternatively, the attachment portion 202 may be separate from the rest of the locking device 200, so that an appropriately sized attachment portion 202 may be used together with common components of the locking device 200 to assemble a locking device 200 adapted for a specific endoscope 150.

The attachment portion 202 may be designed to allow some relative movement of the locking device 200 with respect to the barrel of the endoscope 150. This permits the physician to finely adjust the position and orientation of the guidewire locking device 200 after it has been loosely mounted on the endoscope 150. As will be described below, the specific orientation of the locking device 200 relative to the access port 190 of the endoscope 150 is optimized to provide the best performance. After the locking device 200 has been placed in the correct orientation, it may be immobilized relative to the endoscope 150, for example, by tightening a strap around the endoscope barrel and securing it to a pin 204. In this manner, fine adjustment of the position of the locking device 200 may be obtained, which is then retained to prevent any further movement thereof. The locking device 200 may be attached to endoscope 150 either externally, as shown, or internally, and alternatively may be formed as an integral part of the endoscope 150.

Figure 8:
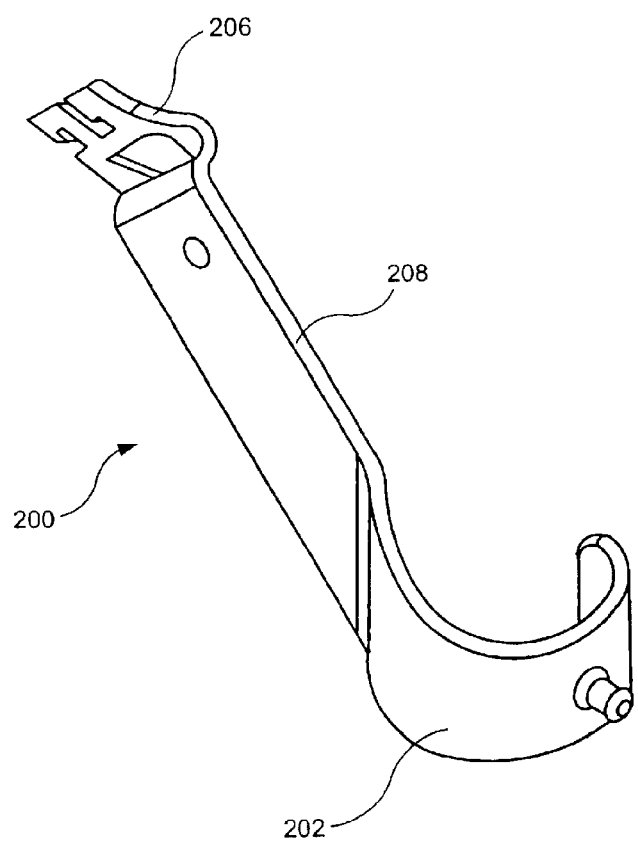
FIG. 8 is a perspective view of the locking arm shown in FIG. 7A.
Figure 9:
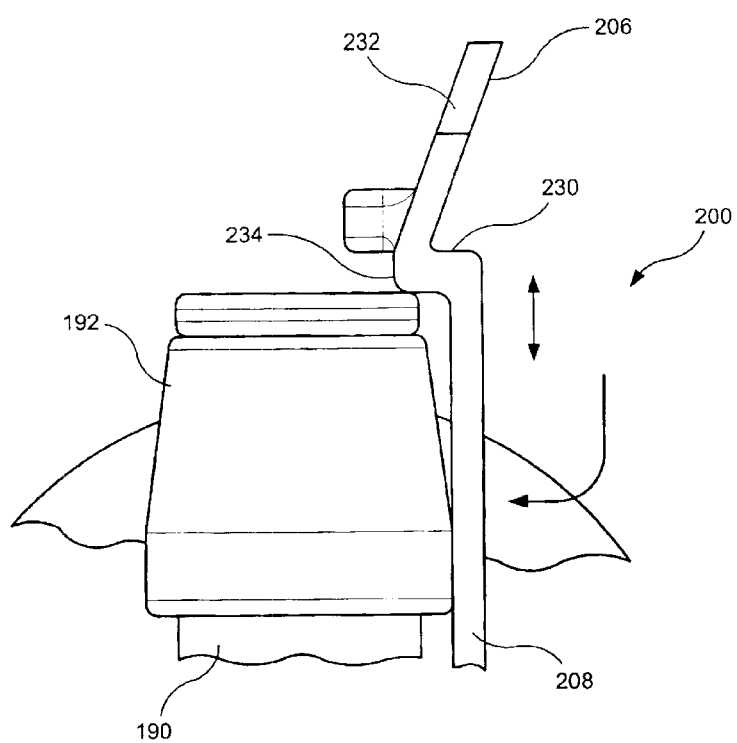
FIG. 9 is a fragmentary perspective view showing a detail of the locking arm mounted on the endoscope, according to the present invention.

Opposite to the attachment portion 202, the locking device 200 shown in FIGS. 7 and 8 includes an angled head 206 which is used to immobilize the guide wire 36 relative thereto. The angled head 206 may preferably be formed at the end of a substantially rigid body 208, which extends from the attachment portion 202. The rigid body 208 has a length and a shape that may vary according to the type of endoscope 150 used in the procedure. According to the invention, the rigid body 208 is shaped so as to place the angled head 206 in proximity to the opening of access port 190, substantially adjacent to the center of a biopsy channel of the endoscope 150. As shown in FIG. 9, the length of the body 208 is sufficient to reach the access port 190, and largely depends on the precise location where the attachment portion 202 connects to the endoscope 150, and on how far the access port 190 extends from the endoscope body. Accordingly, different designs of the rigid body 208 may be provided to fit different endoscopes. The locking device 200 may be made of metal or of polymeric materials which have sufficient stiffness to prevent unwanted movement of the angled head 206 during use. For example, thermoplastic polymers, thermoset polymers or other composites may be used to form the locking device 200. In one embodiment, a biopsy cap 192 is attached to the opening of the access port 190, to prevent contamination by foreign materials and to prevent spilling of bodily fluids from the port. In that case, the locking device 200 is sized to take into account the dimensions of the biopsy cap 192.

The angled head 206 includes many features designed to assist the physician in immobilizing elongated medical members, such as guide wires 36, which exit the endoscope 150 through the access port 190. In particular, multiple locking features 210 are formed on the angled head 206. In the exemplary embodiment shown, two locking features 210 are shown, each of which is capable of independently immobilizing a section of guide wire 36. It will be understood by those of skill in the art that additional locking features may be included, so that more than two guide wires may be locked in place. The number of locking features 210 actually present on a given locking device 200 may vary depending on the intended application, and on the amount of space available on the angled head 206. Alternatively, the locking features 210 may be designed to immobilize other types of elongated medical members. For example, a section of a catheter may be locked in place in the same manner, so that the physician can exchange a guide wire without displacing the catheter from its desired location. As described above, other elements used in endoscopic procedures may be exchanged in the same manner, such as, for example, the sheath assembly 110.

Figure 10:
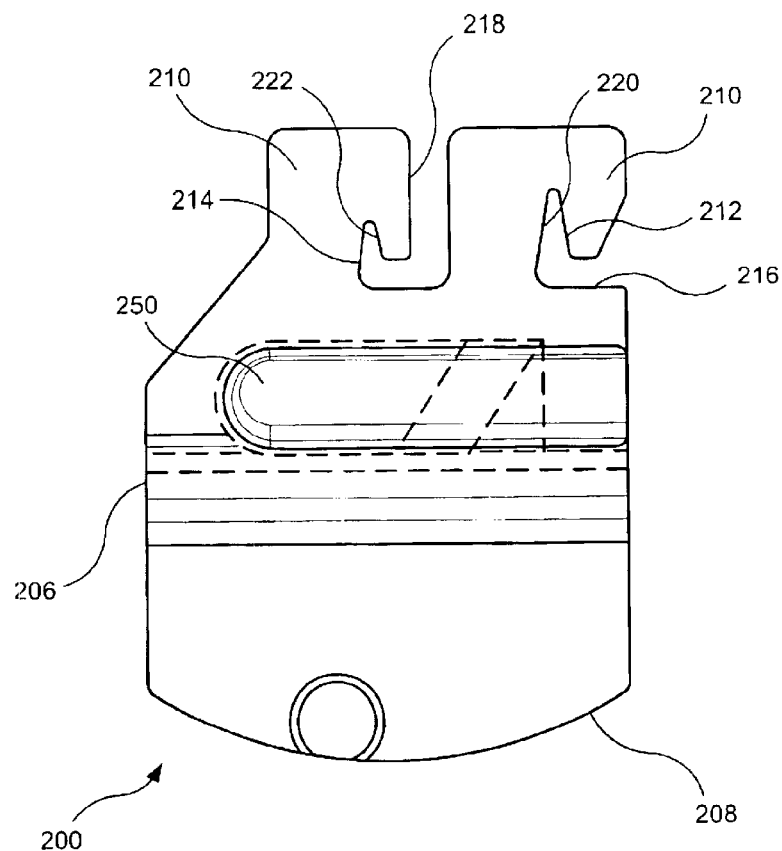
FIG. 10 is an enlarged detail view showing the locking features of the locking arm shown in FIGS. 7A and 8.

As shown in FIG. 10, the locking features 210 operate by frictionally maintaining a section of a guide wire 36 in place. For example, two J-shaped slots 212, 214 may be utilized for that purpose. Exemplary J-shaped slots 212, 214 are formed by entry slots 216, 218 and locking slots 220, 222. During use, a section of the guide wire 36 is inserted in the J-shaped slot 212 via the entry slot 216, and is then pushed by the physician into the locking slot 220 to be immobilized therein. In one example, the entry slot 216 is sufficiently large to allow free movement of the section of the guide wire 36, while the locking slot 220 is tapered to a size smaller than the section of the guide wire 36 to be immobilized, so that when the guide wire 36 is forced therein it is frictionally locked in place by the walls of the locking slot 220. An analogous process may be used to lock a second section of a guide wire 36 in the J-shaped slot 214. The purpose of the entry slots 212, 214 is to separate the multiple guide wires 36, so that each may be immobilized as well as released by the locking features 210 independently of the other. In this manner the physician is given great flexibility in carrying out the procedure.

It will be apparent to those of skill in the art that other, different mechanisms may be employed to immobilize sections of the guide wire 36 in the locking features 210. For example, mechanical features that can bend, compress, twist, pinch or lock the guide wire 36 in place may be used. The J-shaped slots described above are simply one example of a simple, reliable mechanism to effectively lock a section of a guide wire 36 so that the physician's hands are freed to carry out other functions, such as exchanging a catheter associated with the guide wire 36. As shown in FIG. 10, the locking features 210 do not have to be identical, and each may be optimized to immobilize a specific size and type of elongated medical member. For example, the J-shaped slot 212 may be larger than the slot 214, to accommodate a larger guide wire 36 or catheter 34. Different types of locking features 210 may also be intermixed, for example a frictional element such as the J-shaped slot 212 may be combined with another type of mechanical locking feature, without departing from the scope of the present invention.

Figure 11:
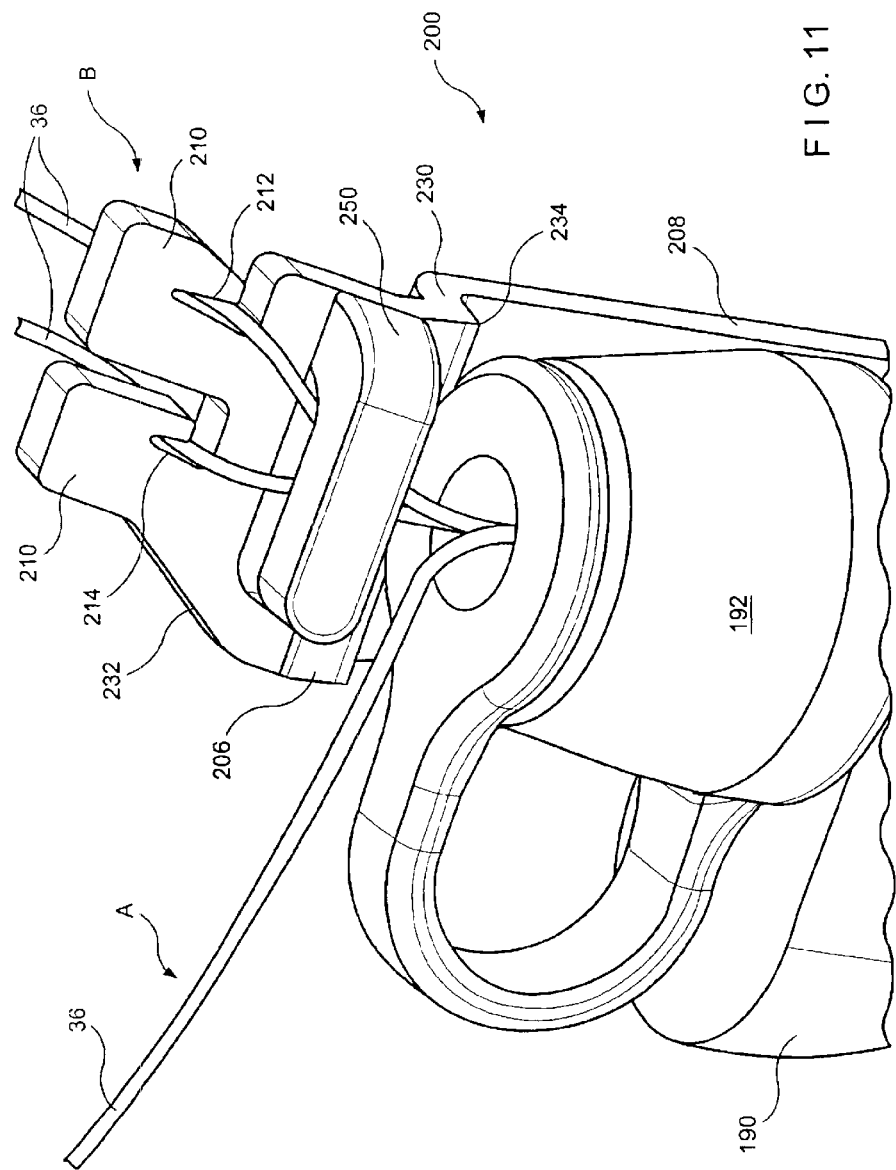
FIG. 11 is a side elevation view showing a detail of the locking arm mounted on the endoscope, according to the present invention.

The angled head 206 is designed to position the locking devices 210 formed thereon in a preferred orientation relative to the access port 190, and consequently relative to the guide wires 36 that exit the endoscope 150 therethrough. As can be seen in FIGS. 9 and 11, the angled head 206 has a first portion 230 that extends towards the opening of the access port 190. If a biopsy cap 192 is installed, this first portion 230 is designed to bring the locking features 210 substantially over the opening of the biopsy channel, so that guide wires 36 can be easily placed in contact with the locking features 210 without excessive manipulation. As discussed above, the specific size and orientation of the first portion 230 depends on the size and shape of the endoscope being used for the procedure. As shown in FIG. 9, the angled head 206 may also include an indexing protrusion 234, which is used to help obtain the correct alignment of the locking features 210 so that they overlie the access port 190. Since, in certain configurations, the locking device 200 may be longitudinally slidable over the endoscope 150 to let the physician fine tune its position, the indexing protrusion 234 may be designed to abut the biopsy cap 192 when the correct longitudinal position is reached.

The angled head 206 includes a second portion 232 that extends away from the opening of the access port 190, at a shallow angle in relation to a longitudinal axis of this opening. In the exemplary embodiment, the locking features 210 are formed on the second portion 232, whose orientation is selected to minimize the curvature of the guide wire(s) 36 as it extends from the access port 190 to the locking features 210. An additional consideration affecting selection of the angular orientation of the second portion 232 is to allow the physician to easily visualize the locking features 210 during the procedure. The more the angled head 206 diverges from the longitudinal axis, the easier it is for the physician to see the locking features 210. This is necessary so that the guide wires 36 can be easily inserted and immobilized in the locking features 210 without distracting the physician from other tasks. The angle at which the angled head 206 diverges from the longitudinal axis of the access port 190 is thus principally selected as a compromise to satisfy the two requirements of a large bending radius for guide wires 36, and of providing to the physician a good view of the locking devices 210. In addition, the angled head 206 is oriented so as not to interfere with the movement of the guide wires 36 when they are not locked in place.

In the exemplary embodiment, a locking arm 250 is provided that extends from the angled head 206. The locking arm 250 is used to further control the bending of the guide wires 36 as they extend from the access port 190 (or the biopsy cap 192) to the locking features 210. The locking arm 250, for example, extends parallel to the surface of the angled head 206, and forms a gap therewith. The guide wires 36 may be inserted in the gap defined by the locking arm 250, and then may be inserted into the locking features 210. The locking arm 250 keeps the guide wires 36 substantially parallel to the angled head 206, so that they do not bow excessively. Keeping the guide wires 36 substantially straight is beneficial, because that retains the greatest amount of column strength to the guide wire 36. If the guide wires 36 are allowed to bow excessively, their column strength is reduced, making them more susceptible to being displaced during the exchange procedure. Also, preventing the guide wire 36 from bowing facilitates the separation of the catheter 34 from the guide wire 36. As will be apparent to those of skill in the art, the locking arm 250 may extend from another portion of the locking device 200, and does not have to be an integral part of the angled head 206.

During an endoscopic operation, a guide wire 36 may, for example, exit the biopsy cap 192, and extend away from the endoscope 150 in an unrestrained position "A", as shown in FIG. 11, to be used to direct a catheter or other medical device to a desired location within a patient's body. As would be understood by those skilled in the art, two or more combinations of catheters and guide wires may be utilized with the same endoscope during a single procedure. If the physician desires to replace one or more catheters 34 without displacing the corresponding guide wire 36, the locking device 200 may be used to immobilize a portion of the guide wire 36, so that it will not be displaced as the catheter 34 is withdrawn and a new catheter 34 is introduced through the endoscope 150. Use of the locking device 200 frees the physician from having to manually hold the guide wire 36 in place while manipulating the old and new catheters. By moving the guide wire 36 into position "B", in engagement with the locking feature 210, the physician can easily exchange the catheter associated with that guide wire 36.

Once the locking device 200 is in position on the endoscope 150, the rigid body 208 of the locking device 200 is placed flush against the side of the access port 190, and the indexing protrusion 234 is moved to abut a top of the biopsy cap 192. The guide wire 36 may then be locked in place. The guide wire 36 is shown in the locked position "B", with a portion thereof held in the gap formed by the locking arm 250 and the surface of the angled head 206, and a section immobilized in the J-shaped slots 212, 214. The slots 212, 214 are aligned relative to the biopsy cap 192 so that the guide wires 36 do not bend excessively. The locking arm 250 further controls the position of the guide wires 36, to prevent them from bowing when they are inserted by the physician in the slots 212, 214. Due to the orientation of the angled head 206, the physician can easily see the slots 212, 214 while performing the procedure, and can easily move the guide wires 36 from the "free" position shown as position "A" to the "locked" position shown as position "B". As described above, the tapered shape of the locking arm 250 and the presence of multiple locking features 210 permit the physician to independently lock and release each of the guide wires 36, and to independently carry out the exchange of the catheters associated with each of those guide wires.

Figure 12:
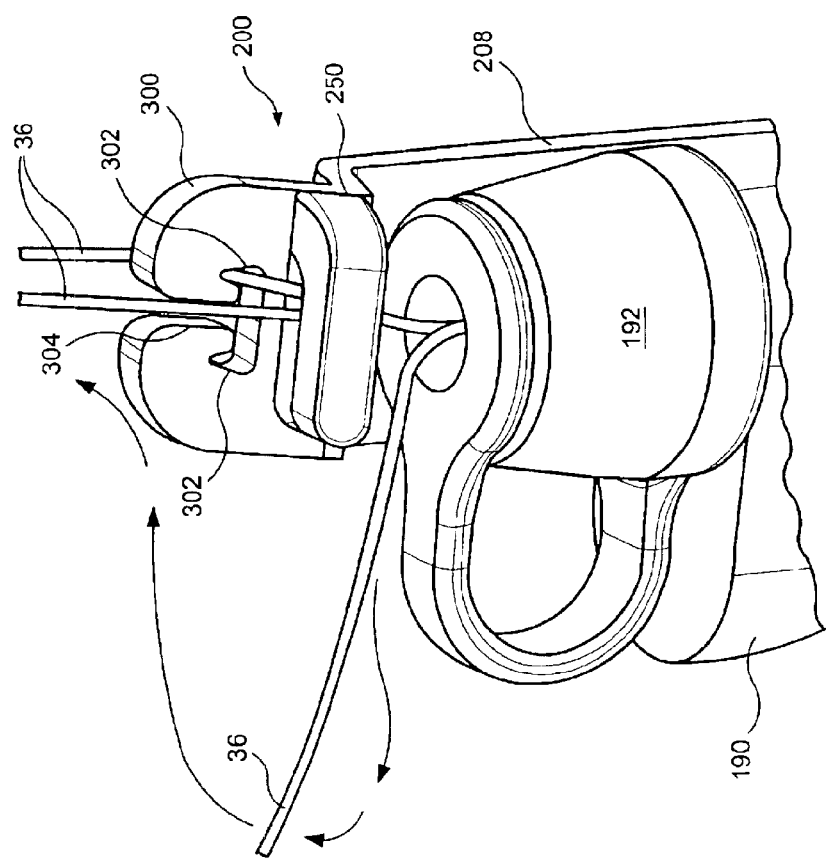
FIG. 12 is a fragmentary perspective view showing a different embodiment of the locking arm mounted on the endoscope, according to the present invention.

FIG. 12 shows a different exemplary embodiment of a locking device 200 according to the present invention. This embodiment includes an angled head 300 with two locking slots 302 that share a common entry slot 304. The position and orientation of the angled head 300 preferably conforms to the same considerations that were discussed with reference to FIGS. 9–11. However, the shape of the locking slots 302 is different. To lock the guide wires 36 in place, the physician inserts each of these guide wires 36 into the entry slot 304, and then further pushes each guide wire 36 into a corresponding one of the locking slots 302, to frictionally retain each guide wire 36 in place within a respective one of the locking slots 302. The locking arm 250 retains the same purpose of preventing excessive bowing of the guide wires 36, and of directing the guide wires 36 towards the locking slots 302 making the device easier to use.

The present invention has been described with reference to specific exemplary embodiments. Those skilled in the art will understand that changes may be made in the details of design of these embodiments, particularly in matters of shape, size, material and the arrangement of the various parts. For example, additional locking features may be provided, and different types of endoscopes and catheters useful in varied procedures may be used. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. A locking device for a maintaining an elongated member at a selected place within a body lumen, the locking device comprising:

a substantially rigid body including an attachment portion adapted to be coupled to a distal portion of a medical instrument wherein, when in an operative position, the distal portion of the medical instrument is received within the body lumen;

an angled head coupled to the substantially rigid body, the angled head being configured to overlie an access port of the medical device when the attachment portion is coupled to the distal portion of the medical device in a predetermined configuration;

a plurality of locking features extending from the angled head to immobilize a section of the elongated member relative to the medical device; and a locking arm extending from the locking device so that, when the attachment portion is coupled to the medical device, the locking arm extends between the access port and the locking features to guide the elongated member from the access port to the locking features along a desired path.

2. The locking device according to claim 1, wherein the locking arm extends from the angled head.

3. The locking device according to claim 2, wherein the angled head is configured to position the locking arm such that a gap formed between the locking arm and the angled head overlies the access port.

4. The locking device according to claim 1, wherein the locking arm is adapted to prevent bowing of the elongated medical member between the access port and the locking features.

5. The locking device according to claim 1, wherein the locking features include gripping surfaces which frictionally immobilize a portion of the elongated member received therein.

6. The locking device according to claim 5, wherein the gripping surfaces are formed along sides of tapered slots with a minimum width each of the slots being less than a diameter of a portion of the elongated medical member to be immobilized thereby.

7. The locking device according to claim 6, wherein the slots comprise an entry slot and a locking slot disposed in a "J" shape.

8. The locking device according to claim 7, wherein the locking arm is oriented to retain a portion of the elongated medical member in a position substantially parallel to the angled head.

9. The locking device according to claim 1, wherein each of the locking features is adapted to independently retain at least one elongated member.

10. The locking device according to claim 1, wherein the locking features comprise mechanical elements to apply at least one of a compression, bending and pinching force to the elongated medical member.

11. The locking device according to claim 1, wherein the locking arm is tapered to allow independent limited movement of two elongated members simultaneously.

12. The locking device according to claim 1, wherein the angled head includes a position indexing protrusion extending therefrom to indicate a correct positioning thereof relative to the access port.

13. The locking device according to claim 1, wherein the angled head extends to a position substantially overlying the access port, to minimize bending of the elongated member between the access port and the locking features.

14. The locking device according to claim 1, wherein the elongated member is a guide wire.

15. The locking device according to claim 1, wherein the medical device is an endoscope.

16. A locking device for maintaining a position within a body lumen of a first elongate member relative to a flexible endoscope while a second elongate member is withdrawn from the body lumen, the locking device comprising:

a mounting mechanism for selectively coupling the locking device to a distal end of the endoscope;

an angled head which, when the mounting mechanism is coupled to the endoscope in a predetermined configuration, overlies an opening at a distal end of the endoscope to a working channel of the endoscope;

a plurality of locking features extending from the angled head to immobilize a portion of the first elongate member relative to the endoscope; and a locking arm extending from the angled head between the opening at the distal end of the endoscope and the locking features to limit movement of a portion of the first elongate member between the opening and the locking features.

17. The system according to claim 16, wherein a first one of the locking features includes a frictional engagement surface for gripping the first elongate member.

18. The system according to claim 16, wherein a first one of the locking features includes an entry slot and a locking slot operatively connected thereto, the entry slot having a size greater than a diameter of a portion of the first elongate member to be immobilized thereby wherein a portion of the locking slot has a size smaller than the diameter of the portion of the first elongate member to be immobilized thereby.

19. The system according to claim 18, wherein the locking slot and the entry slot are disposed in a substantially "J-shaped" configuration.

20. The system according to claim 16, wherein the angled head is configured so that, when the mounting mechanism is coupled to the endoscope in a predetermined configuration, the locking features overlie the opening.

21. The system according to claim 16, wherein the locking arm is oriented to retain the portion of the first elongate member extending between the opening and the locking features substantially parallel to the angled head.

22. The system according to claim 16, further comprising an endoscope sheath assembly which slidably receives the catheter therein, the endoscope sheath being sized to be inserted through the working channel of the endoscope.

23. A method of performing a medical procedure, comprising the steps of:

inserting an endoscope into a body lumen;

inserting a distal end of a first elongate member into the lumen via the access port so that a proximal portion of the first elongate member extends from proximally from the access port;

providing a locking device at a distal end of the endoscope;

immobilizing a portion of the first elongate member relative to the endoscope by engaging a first locking feature of the locking device with the first elongate member; and engaging a locking arm of the locking device with the first elongate member to direct the first elongated medical member along a first predetermined path from the distal end of the endoscope to the first locking feature.

24. The method according to claim 23, further comprising inserting the first elongate member into a lumen of a second elongate member and inserting the second elongate member in the endoscope, whereby the first elongate member extends within the lumen from an access port thereof a distal opening of the second elongate member.

25. The method according to claim 24, further comprising the step of exchanging the second elongate member without displacing the first elongate member immobilized by the first locking feature.

26. The method according to claim 25, wherein the locking device comprises a second locking feature, the method further comprising the steps of:

immobilizing a portion of the third elongate member relative to the endoscope by engaging a second locking feature with the third elongate member; and engaging the locking arm with the third elongate member to direct the third elongated medical member along a second predetermined path from the distal end of the endoscope to the second locking feature.

* * * * *